(12) United States Patent
Gordon

(10) Patent No.: US 12,178,478 B2
(45) Date of Patent: *Dec. 31, 2024

(54) DEVICE AND METHOD FOR TREATMENT OF SPINAL DEFORMITY

(71) Applicant: GLOBUS MEDICAL, INC., Audubon, PA (US)

(72) Inventor: Jeffrey David Gordon, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 254 days.

This patent is subject to a terminal disclaimer.

(21) Appl. No.: 17/962,605

(22) Filed: Oct. 10, 2022

(65) Prior Publication Data

US 2023/0031742 A1 Feb. 2, 2023

Related U.S. Application Data

(63) Continuation of application No. 16/919,153, filed on Jul. 2, 2020, now Pat. No. 11,464,550, which is a continuation of application No. 15/967,690, filed on May 1, 2018, now Pat. No. 10,716,598, which is a continuation of application No. 15/620,953, filed on Jun. 13, 2017, now Pat. No. 9,987,049, which is a continuation of application No. 11/893,173, filed on Aug. 16, 2007, now Pat. No. 9,717,537, which is a continuation-in-part of application No. 11/215,725, filed on Aug. 30, 2005, now Pat. No. 7,763,053.

(60) Provisional application No. 60/605,548, filed on Aug. 30, 2004.

(51) Int. Cl.
*A61F 2/44* (2006.01)
*A61B 17/58* (2006.01)
*A61B 17/70* (2006.01)

(52) U.S. Cl.
CPC .......... *A61B 17/7055* (2013.01); *A61B 17/58* (2013.01); *A61B 17/7016* (2013.01); *A61B 17/7022* (2013.01); *A61B 17/7053* (2013.01)

(58) Field of Classification Search
CPC ............ A61B 17/7055; A61B 17/7016; A61B 17/7014; A61B 17/7017
See application file for complete search history.

(56) References Cited

U.S. PATENT DOCUMENTS

| 2,702,031 | A | * | 2/1955 | Wenger | .............. | A61B 17/7055 |
| | | | | | | 606/51 |
| 3,680,553 | A | | 8/1972 | Seppo | | |
| 4,157,715 | A | | 6/1979 | Westerhoff | | |

(Continued)

OTHER PUBLICATIONS

Excerpts from Gordon, Jeff, "Active Internal Fixation: Characterization of Two Original Intramedullary Nail Designs." Thesis submitted to the Faculty of the Graduate School of Vanderbilt University, May 1996.

*Primary Examiner* — Jan Christopher L Merene

(57) ABSTRACT

The present invention generally relates to methods and devices for treatment of spinal deformity, and in particular to the utilization of at least one implant to either maintain the position of at least one vertebra of a patient to prevent increase in abnormal spinal curvature, to slow progression of abnormal curvature, or to impose at least one corrective displacement and/or rotation on at least one vertebra of a patient so as to incrementally correct abnormal spinal curvature.

15 Claims, 17 Drawing Sheets

(56) References Cited

U.S. PATENT DOCUMENTS

| | | |
|---|---|---|
| 4,262,665 A | 4/1981 | Roalstad et al. |
| 4,384,373 A | 5/1983 | Sivash |
| 4,453,539 A | 6/1984 | Raftopoulos et al. |
| 4,502,160 A | 3/1985 | Moore et al. |
| 4,892,546 A | 1/1990 | Kotz et al. |
| 5,074,882 A | 12/1991 | Grammont et al. |
| 5,505,733 A | 4/1996 | Justin et al. |
| 5,704,939 A | 1/1998 | Justin |
| 2004/0030395 A1* | 2/2004 | Blunn ................ A61B 17/7016 623/23.45 |
| 2004/0193266 A1* | 9/2004 | Meyer ...................... A61F 2/46 623/16.11 |
| 2006/0004459 A1* | 1/2006 | Hazebrouck ............. A61F 2/36 623/23.45 |

\* cited by examiner

Section A-A

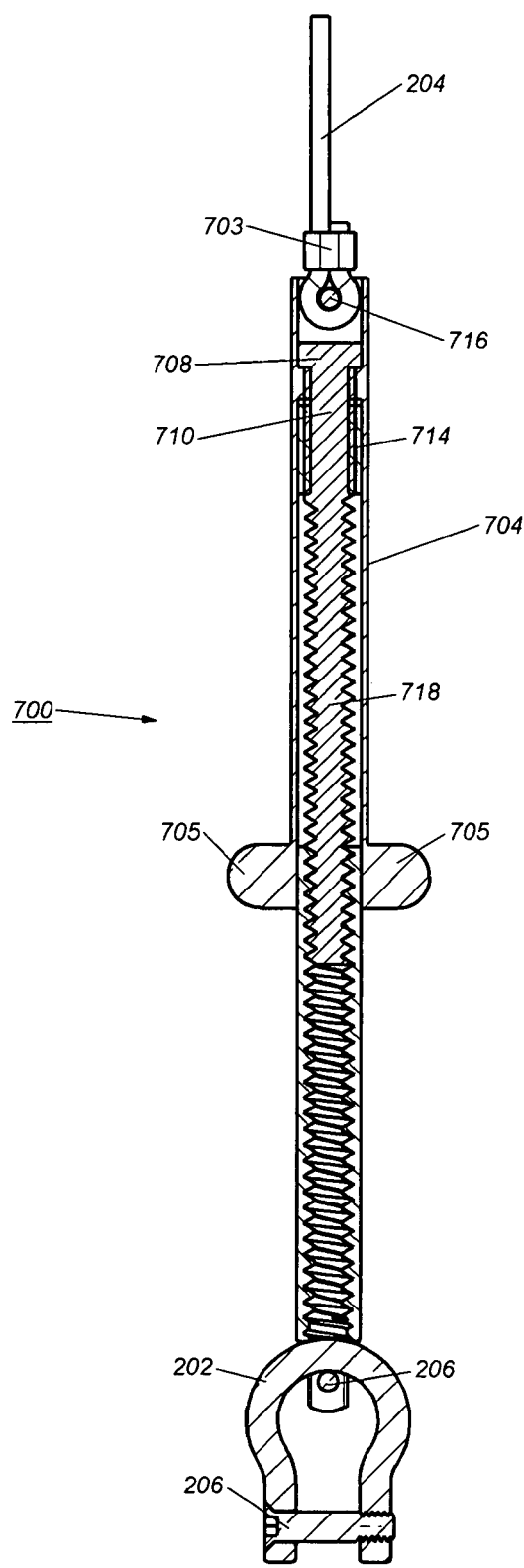
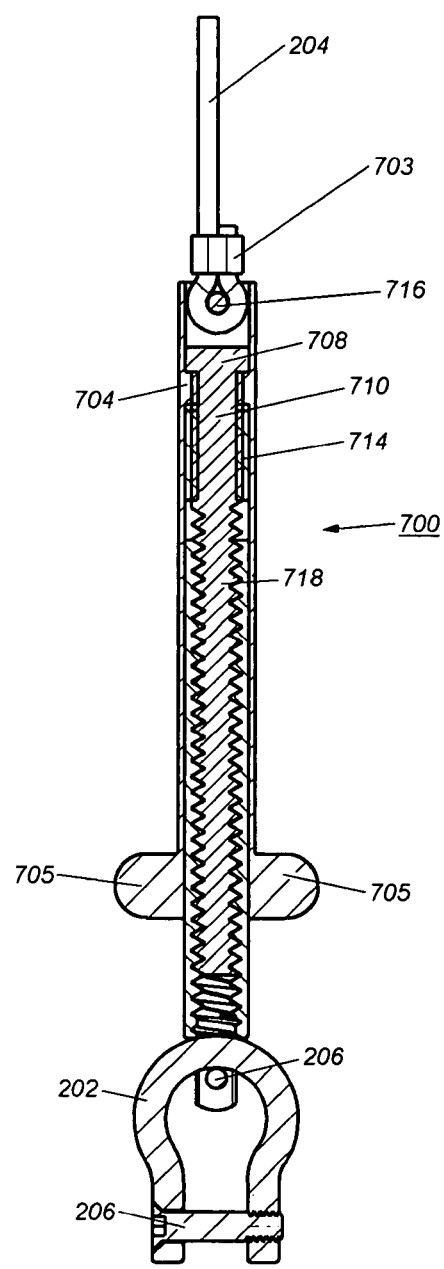
Fig. 18A
Fig. 18B

DEVICE AND METHOD FOR TREATMENT OF SPINAL DEFORMITY

REFERENCE TO RELATED APPLICATIONS

This application is a continuation of U.S. patent application Ser. No. 16/919,153, filed Jul. 2, 2020, which is a continuation of U.S. patent application Ser. No. 15/967,690, filed May 1, 2018, which is a continuation of U.S. patent application Ser. No. 15/620,953, filed Jun. 13, 2017, which is a continuation of U.S. patent application Ser. No. 11/893,173, filed Aug. 16, 2007, now issued as U.S. Pat. No. 9,717,537, which is a continuation-in-part of U.S. patent application Ser. No. 11/215,725, filed Aug. 30, 2005, now issued as U.S. Pat. No. 7,763,053, which claims the benefit, pursuant to 35 U.S.C. § 119(e), of U.S. Provisional Application 60/605,548, filed Aug. 30, 2004, entitled "IMPLANT FOR CORRECTION OF SPINAL DEFORMITY," the contents of which are all incorporated herein in their entireties by reference, respectively, for all purposes.

FIELD OF THE INVENTION

The present invention generally relates to methods and devices for treatment of spinal deformity.

BACKGROUND OF THE INVENTION

Scoliosis is a spinal deformity characterized by an abnormal curvature of the spine in the coronal plane and is often associated with an abnormal rotation in the axial plane causing ribs to protrude posteriorly into what is commonly referred to as "rib hump". Adolescent idiopathic scoliosis (AIS) is the most prevalent type of scoliosis which develops during adolescence in an otherwise healthy patient and typically ceases at the onset of skeletal maturity. The cause of the disease is presently unknown.

Current surgical treatment of scoliosis involves manipulation of the spinal column and attachment of corrective devices for fusion of a portion of the spine. One such system, the Cotel-Dubousset system, disclosed in U.S. Pat. No. 5,147,360 to Dubousset, utilizes rigid metal rods attached to the spine. The rods are manipulated during surgery in an attempt to reduce abnormal curvatures and rotations of the spinal column. Typically, extensive discectomies are necessary, as well as removal of the spinous processes and injury to the spine itself to induce bleeding to aid bone fusion. The spine is then fused with bone graft harvested from the patient's illium or from a bone bank.

The surgery is arduous, invasive, and has an array of potential complications. Large loads are exerted on the spine for correction [1] which risks the patient's neurological condition. A long incision is required and extensive bone graft is harvested, therefore excessive blood loss can occur. Recovery can be a lengthy and painful process. If normal lordosis and kyphosis are not restored, a condition called "flat back syndrome", the patient may have chronic pain. Even a successful procedure rarely results in a normal spinal curvature and the patient is left with an immobile spinal section. The discs above and below the fusion zone are in jeopardy of degeneration due to the increased biomechanical demands placed on them. In general, it is a major surgery with the possibility of major complications.

Therefore, it is evident there are flaws in prior art methods and devices. Most prior art devices are part of the load path of the spinal column. For example, it is understood that the Cotel-Dubousset system rigidly attaches stiff stainless steel rods to the spine. A structure having two roughly parallel support members relies primarily on the stiffer of the two members for transmission of loads. Therefore, loads exerted on an instrumented spine are transferred through the implant instead of through the spine. Spinal loads can be significantly large, and the geometry of the implants used is such that they will not support such loads indefinitely. Fatigue failure of the implant will occur if fusion is delayed.

The mechanical properties of spinal structures such as the intervertebral discs, ligaments, nerves and muscles have a time-dependent relationship between force and displacement, a characteristic called viscoelasticity. Viscoelastic structures increase strain under the action of an applied constant stress (creep) and decrease internal stress under the action of an applied constant strain (stress-relaxation). It has been shown that dramatic stress-relaxation occurs over time in patients who have undergone scoliosis correction surgery involving stiff metal rods. However, the stiffness of the rods prevents them from taking advantage of this phenomenon.

U.S. Pat. No. 5,490,851 to Nenov et al. describes a pelvis alignment device which rigidly attaches to the pelvis to align the pelvic girdle. After alignment with this device, artificial joints are used to hold the pelvis and sacrum in the aligned position. Flexible cords with worm gear drive members are attached so that "force is applied to the distorted spine so that it does not tend to act against the effects of the joints". Therefore, the flexible cords work in conjunction with the artificial joints to maintain alignment correction achieved with a pelvis alignment device.

U.S. Pat. No. 6,849,076 to Blunn et al. describes a group of magnet driven devices for surgical distraction. A device for correction of scoliosis is described which is attached to two vertebrae and is non-invasively distracted by an external changing magnetic field.

U.S. Pat. No. 6,299,613 to Ogilvie et al. describes a tether connected to points on the spine to maintain a curvature, or to constrain growth of the convex side of the spine.

Therefore, a heretofore unaddressed need exists in the art to address the aforementioned deficiencies and inadequacies.

SUMMARY OF THE INVENTION

The current invention describes a method and devices for treating spinal deformity which offers significant improvements over prior art methods and devices. Treatment of spinal deformity, such as scoliosis, includes: preventing or reducing progression of an abnormal spinal curvature prior to fusion, preventing or reducing progression of an abnormal spinal curvature without fusion, correction of an abnormal spinal curvature prior to fusion, correction of an abnormal spinal curvature without fusion, or maintenance or improvement of a surgically corrected spinal curvature.

In general terms the concept behind the present invention is introduction of tension between the pelvis and spine to either correct or maintain spinal deformity. The tension force may take the form of a maintained or incrementally reduced length between at least one point on the spine and at least one point on the pelvis which will consequently produce a resisting tension force when acted against by the patient's musculature. There are many embodiments of the invention which will achieve the stated objectives, some of which will be presented in the following summary.

In one embodiment of the invention, at least one device is attached between the spine and the pelvis which incorporates at least one flexible tether such as a twisted (helically wound, or laid) wire rope, braided wire rope, twisted non-metallic rope, braided non-metallic rope, a rope consisting of metallic and non-metallic fibers, multiple strand wire, single strand wire, multiple strand polymer, single strand polymer, Kevlar, link chain, bead chain, or a metallic or non-metallic tape. Alternatively, the tether could be a rigid rod or telescoping tubes which contracts but has an adjustable stop to limit extension.

Attachment of the flexible tether to the spine and/or pelvis might involve a loop of material placed around a boney structure (e.g. the spineous process), or a hole through a boney structure through which the flexible tether is passed. Alternatively, it may be necessary to implant attachment means at the spine attachment site(s) and/or the pelvis attachment site(s) and then attach the tether to the attachment means. For example, at least one bone screw, cannulated bone screw, clamp, plate, bone anchor, or shackle might be attached to at least one vertebra or pelvic bone and the flexible tether may be attached to it. Other means of attachment will be clear to one practiced in the art.

The tether can branch into multiple tethers to provide multiple attachments to the spine and/or pelvis. If more than one tether is used, each can be attached to a different vertebra, or multiple tethers can be attached to the same vertebra. Tethers can be attached to either or both sides of the vertebra and either or both pelvic bones as needed to generate correction of the spinal deformity. A crossing pattern whereby a tether is attached to the right side of the vertebra (e.g. the right pedicle) and left pelvic bone, or vice versa, is possible. Also, a tether may be attached to a vertebra and then passed through an eye screw or other guiding device which is attached to the pelvic bones and then attached to a second vertebra with a pedicle screw or other means. It can be envisioned by one skilled in the art that guiding devices may be utilized on a number of vertebrae or on the pelvis. The tether may also originate with an attachment to the pelvis, pass through any number of guide members attached to the spine, and then terminate at the pelvis again.

In another embodiment of the invention, any of the above described devices may incorporate a means to shorten the overall length of the device. Taking advantage of the inherent viscoelasticity of spinal structures, the curvature is gradually corrected by small incremental corrections over a protracted period of time. In one embodiment, the means to shorten the device is a changing magnetic field. In another embodiment, the means to shorten the device is a toggle which can be manipulated by pressing on the patient's skin. In another embodiment, shortening the device requires an incision so that the device can be manipulated directly.

These and other aspects of the present invention will become apparent from the following description of the embodiments taken in conjunction with the following drawings, although variations and modifications therein may be affected without departing from the spirit and scope of the novel concepts of the disclosure.

Objects of the Present Invention

It is an object of the present invention to provide an improved method of arresting the progression of spinal deformity whereby at least one device is surgically attached to the spine and to a boney structure other than the spine, such as the pelvis.

It is another object of the present invention to provide an improved method of correcting a spinal deformity whereby at least one device is surgically attached to the spine and to another boney structure other than the spine, such as the pelvis; the device being capable of being shortened to impose at least one incremental correction over a period of time.

It is another object of the present invention to provide an improved method of correcting a spinal deformity with at least one device which is surgically attached to the spine and to another boney structure other than the spine, such as the pelvis, the device being capable of being shortened to impose at least one incremental correction over a period of time and which is actuated by a non-invasive method such as with a changing magnetic field or by pressing on the exterior surface of the patient's skin.

BRIEF DESCRIPTION OF THE DRAWINGS

FIG. 18A shows a sectioned view of the device shown in FIGS. 17A and 17B in an extended or "lengthened" configuration.

FIG. 18B shows a sectioned view of the device shown in FIGS. 17A and 17B in a retracted or "shortened" configuration.

DETAILED DESCRIPTION OF THE EMBODIMENTS

Figure 1:
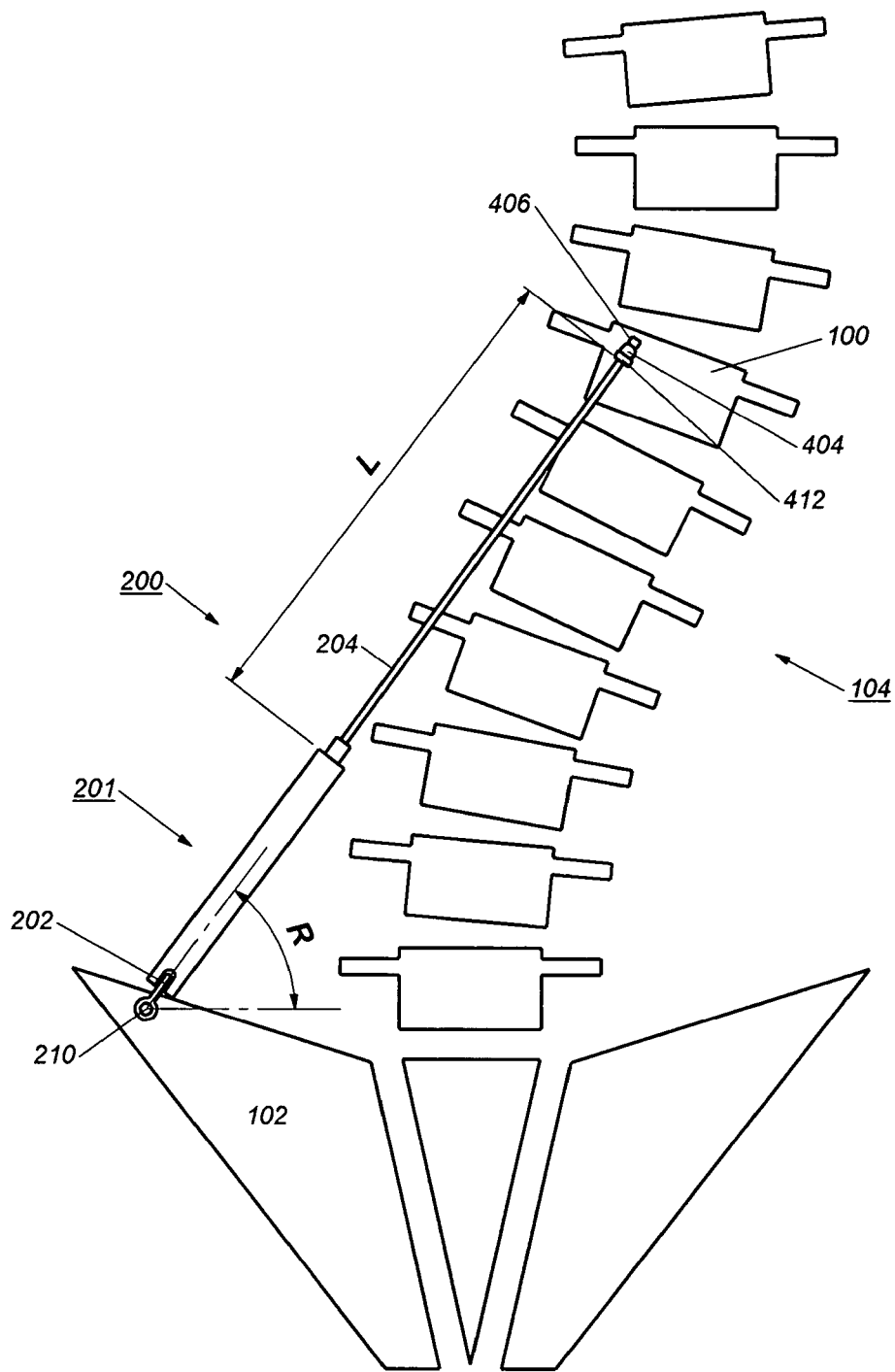
FIG. 1 shows schematically a posterior view of a deformed human spine with an implanted device according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The description will be made as to the embodiments of the present invention in conjunction with the accompanying drawings. In accordance with the purposes of this invention, as embodied and broadly described herein, this invention, in one aspect, relates to an implant for surgical treatment of abnormal spinal curvature by imposing restraints or corrective displacements to spinal vertebrae. For ease of understanding, the present invention is described with specific reference to scoliosis. However, the present invention disclosed herein is generally applicable to all classifications of spinal curvature disorders, including but not limited to hyper-lordosis, hyper-kyphosis, sagittal imbalance, and coronal imbalance.

FIG. 1 is a schematic representation of a posterior view of a deformed spine 104 whereby one embodiment of the device 200 is attached to a pelvic bone 102 and a vertebra 100 of a patient. The device 200 includes an actuation means 201, and a connection means 204. Attachment of actuation means 201 to pelvic bone 102 is shown with a shackle 202 attached through a hole 210 created in pelvic bone 102. Attachment of connection means 204 to vertebra 100 is shown with a pedicle screw 412, a ball 404 and a crimp 406. The initial angle of device 200 relative to horizontal is shown as R and the initial length of the exposed portion of connection means 204 is shown as L. More detailed drawings and descriptions follow.

Figure 2:
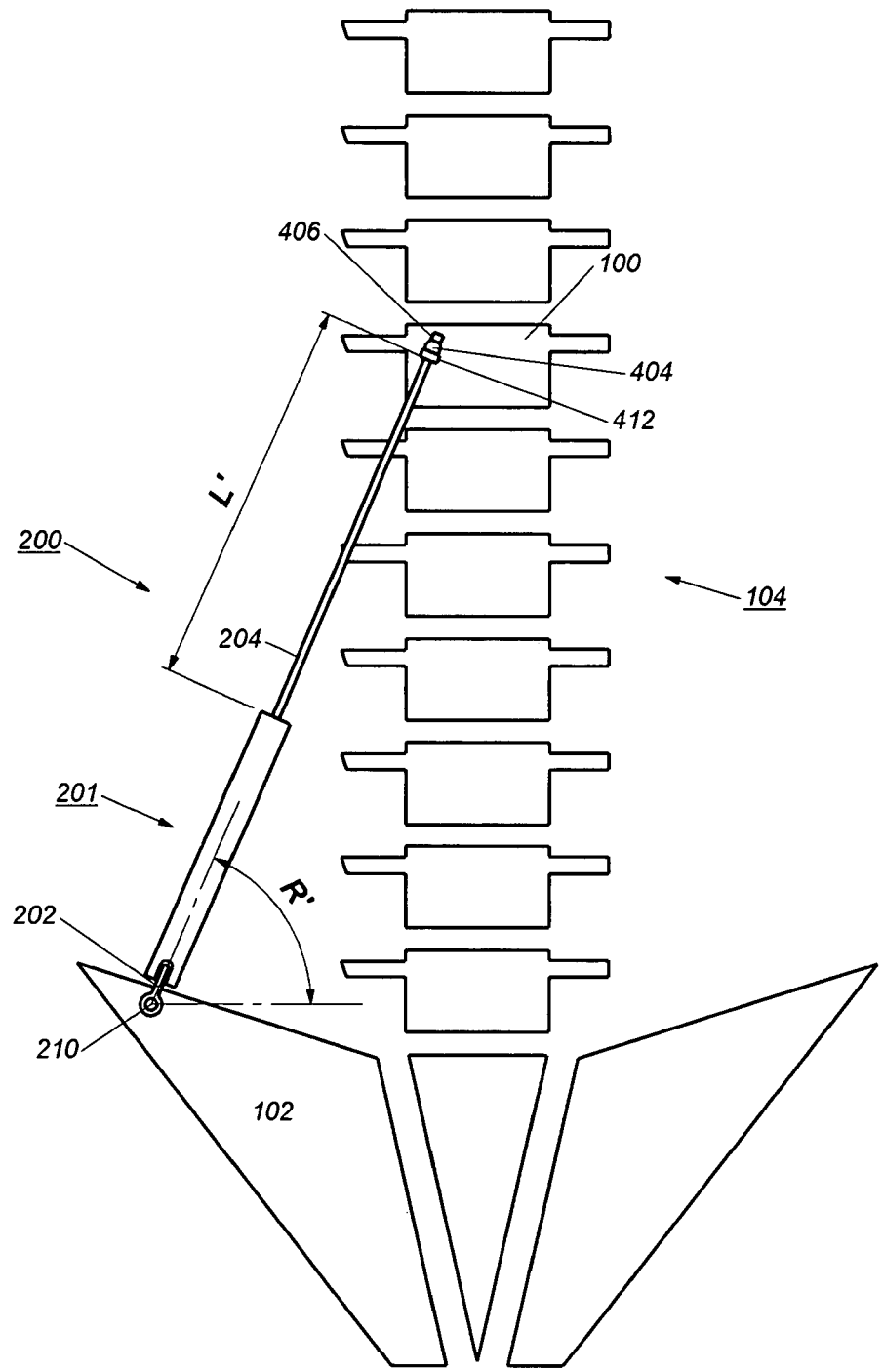
FIG. 2 shows schematically a posterior view of a corrected human spine with the implanted device shown in FIG. 1.

FIG. 2 is a schematic representation of a posterior view of the patient's spine 104 after correction of the abnormal spinal curvature with the implanted device 200. In this figure, actuation means 201 has shortened the overall length of device 200 by pulling connection means 204 into actuation means 201 so that the exposed length L' of connection means 204 is significantly shorter than the original exposed length L shown in FIG. 1. Also, the angle of device 200 relative to horizontal, represented by R', is greater than the original angle R in FIG. 1.

Figure 3:
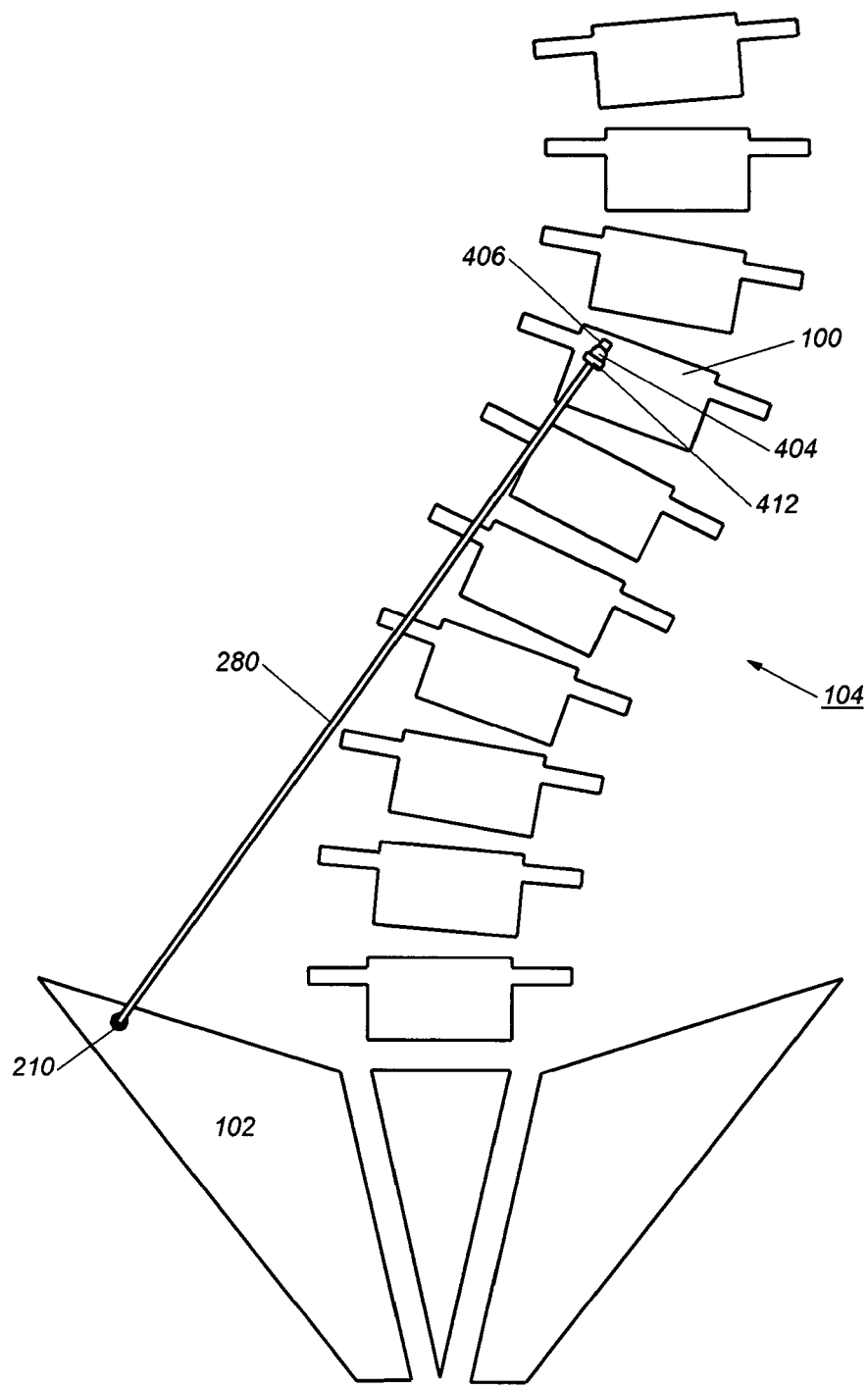
FIG. 3 shows schematically a posterior view of a deformed human spine with an implanted device according to another embodiment of the present invention.

FIG. 3 is a schematic representation of an alternative embodiment of the invention, whereby a tether 280 is attached to vertebra 100 and to pelvic bone 102, but does not have an actuation member. This embodiment can be used to prevent progression of spinal deformity, or can be shortened manually with an incision at either the pelvic bone 102, or vertebra 100 attachment sites, or both, to correct a curvature. Preferably tether 280 is a wire rope, a cord or other such device as stated earlier. Alternatively, tether 280 can be a rigid member.

Figure 4:
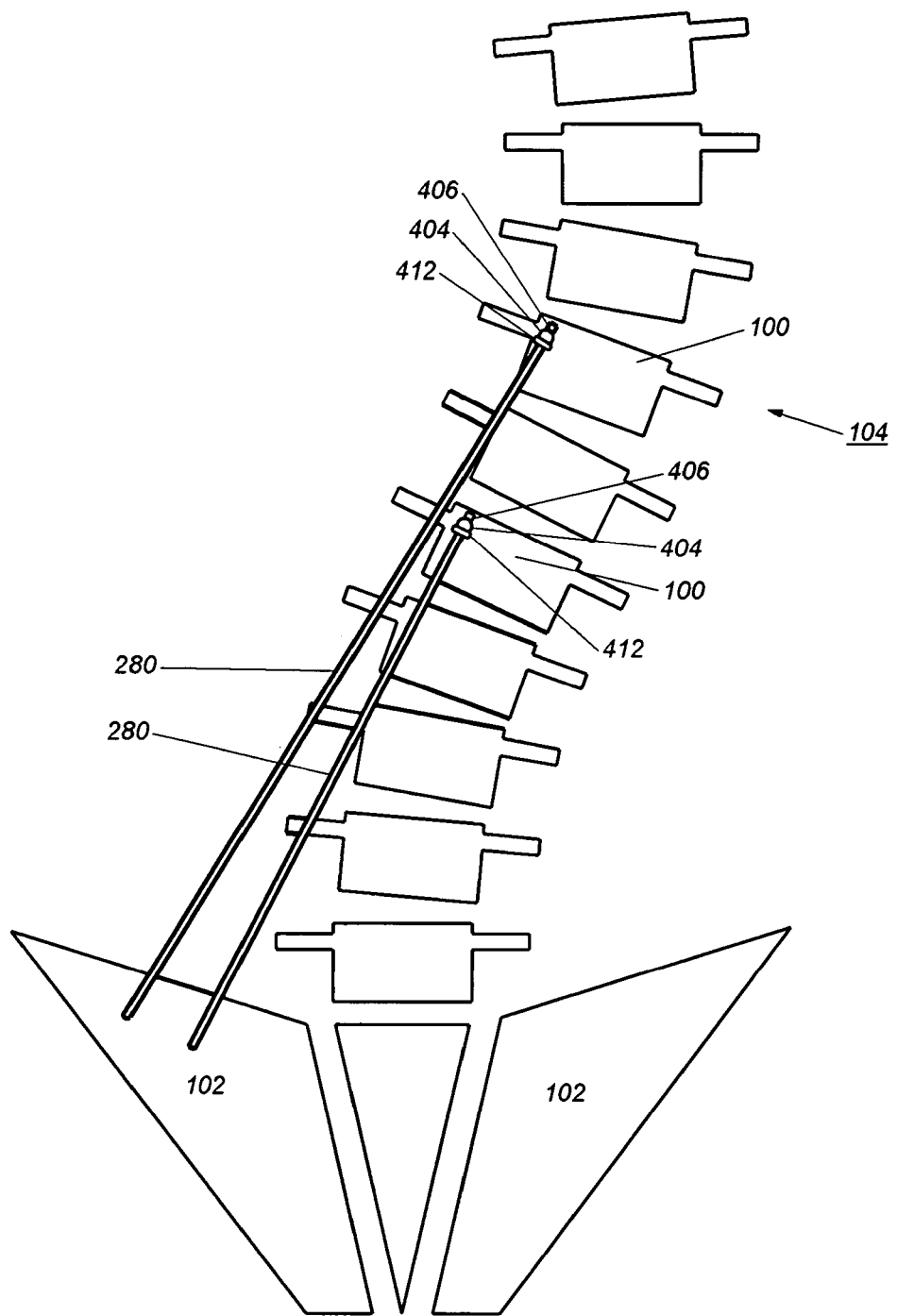
FIG. 4 shows schematically a posterior view of a deformed human spine with multiple implanted devices according to another embodiment of the present invention.

FIG. 4 is a schematic representation of another alternative embodiment of the invention whereby multiple tethers 280 are utilized. Each tether 280 can be attached to a different vertebra 100 as shown, or multiple tethers 280 can be attached to the same vertebra 100. Alternatively, each tether 280 may branch into multiple tethers at one or both ends to provide multiple attachment means for each tether. Tethers 280 can be attached to either or both sides of the vertebra 100 and either or both pelvic bones 102 as needed to generate correction of the spinal deformity. A crossing pattern whereby a tether 280 is attached to the right side of the vertebra 100 (e.g. the right pedicle) and left pelvic bone 102, or vice versa, is possible. Attachment to the spineous process is also possible. Also, tethers 280 may be attached to a pelvic bone 102, passed through a guiding device (e.g. an eye screw or other guiding device through which tethers 280 may slide) which is attached to a vertebra 100, and then attached to a second vertebra 100 with a pedicle screw or other means, or it may terminate at the same or the opposite pelvic bone 102. It can be envisioned by one skilled in the art that guiding devices may be utilized on a number of vertebrae to correct spinal deformity.

Figure 5:
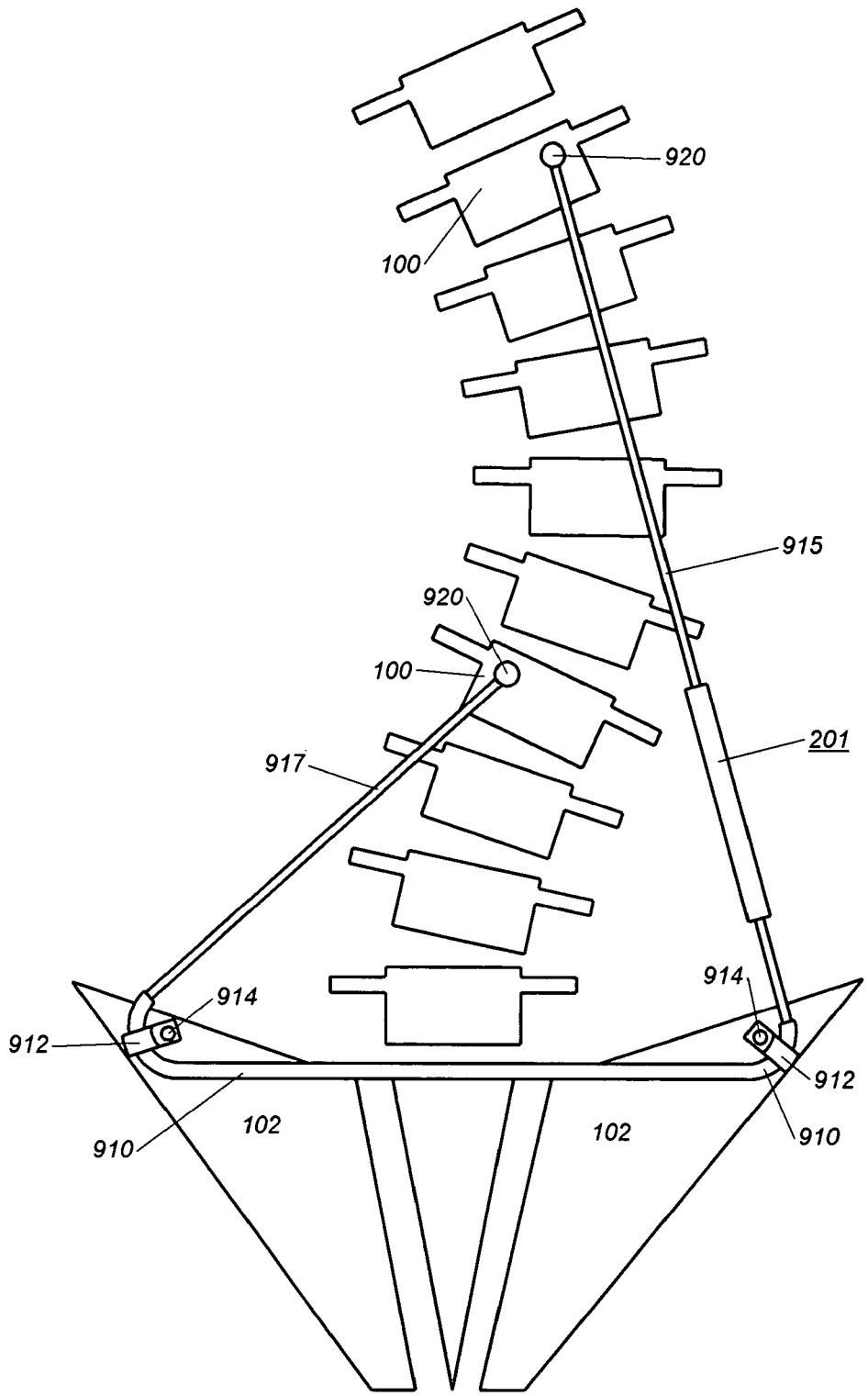
FIG. 5 shows schematically a posterior view of a deformed human spine with an implanted device according to another embodiment of the present invention.

FIG. 5 is a schematic representation of another alternative embodiment of the invention whereby a first flexible member 915 is attached to a first vertebra 100 with a vertebral anchoring means 920; a second flexible member 917 is attached to a second vertebra 100 with a vertebral anchoring means 920; and a sheath 910 is attached to at least one pelvic bone 102 with at least one bracket 912 secured with at least one bone screw 914. First flexible member 915 is attached to an actuation means 201 which is capable of invasively, or non-invasively contracting as described above. Second flexible member 917 is passed through sheath 910 and then attached to actuation means 201. Second flexible member can preferably slide within sheath 910 with minimal friction, thereby reducing or eliminating abrasion to second flexible member 917 and/or pelvic bone 102 and the sacrum. Actuation of actuation means 201 will shorten the overall length of the entire device by pulling either first flexible member 915 or second flexible member 917 into its housing. This shortening will impose a corrective displacement and/or force on the deformed spine, while preferably allowing some motion of the spine for daily activities. Multiple first flexible members 915, second flexible members 917, sheaths 910 and/or actuation means 201 can be utilized to correct the deformity.

Figure 6A:
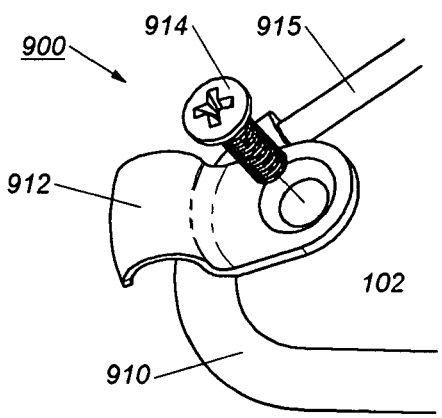
FIG. 6A is an exploded, detail view of one embodiment of a guide means.
Figure 6B:
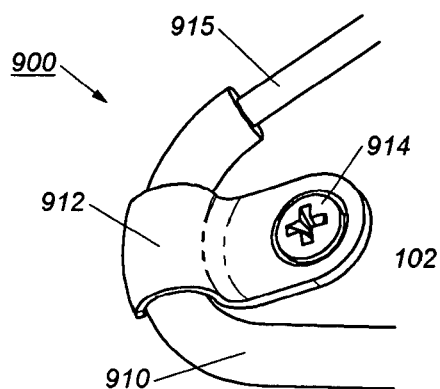
FIG. 6B is a detail view of one embodiment of a guide means.
Figure 7A:
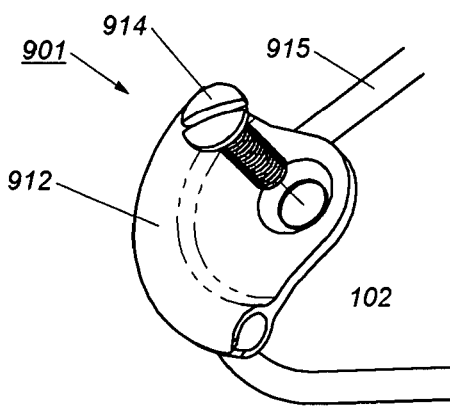
FIG. 7A is an exploded, detail view of another embodiment of a guide means.
Figure 7B:
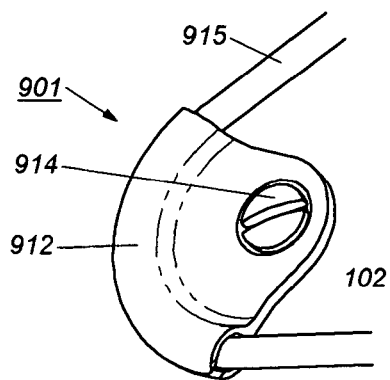
FIG. 7B is a detail view of another embodiment of a guide means.
Figure 8A:
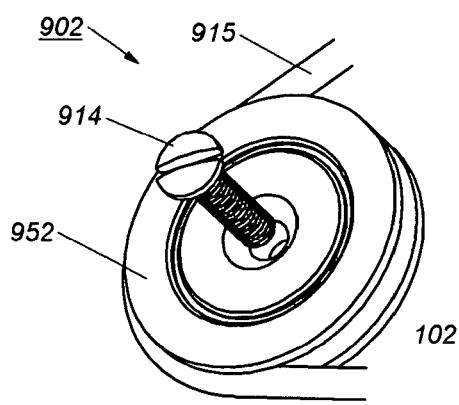
FIG. 8A is an exploded, detail view of another embodiment of a guide means.
Figure 8B:
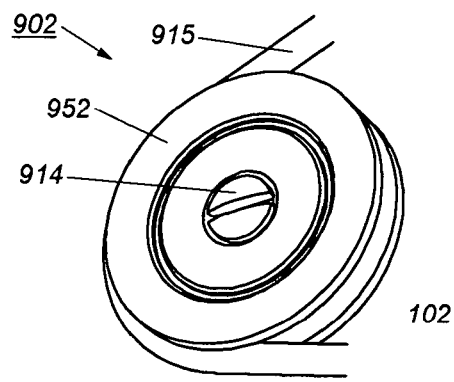
FIG. 8B is a detail view of another embodiment of a guide means.
Figure 9A:
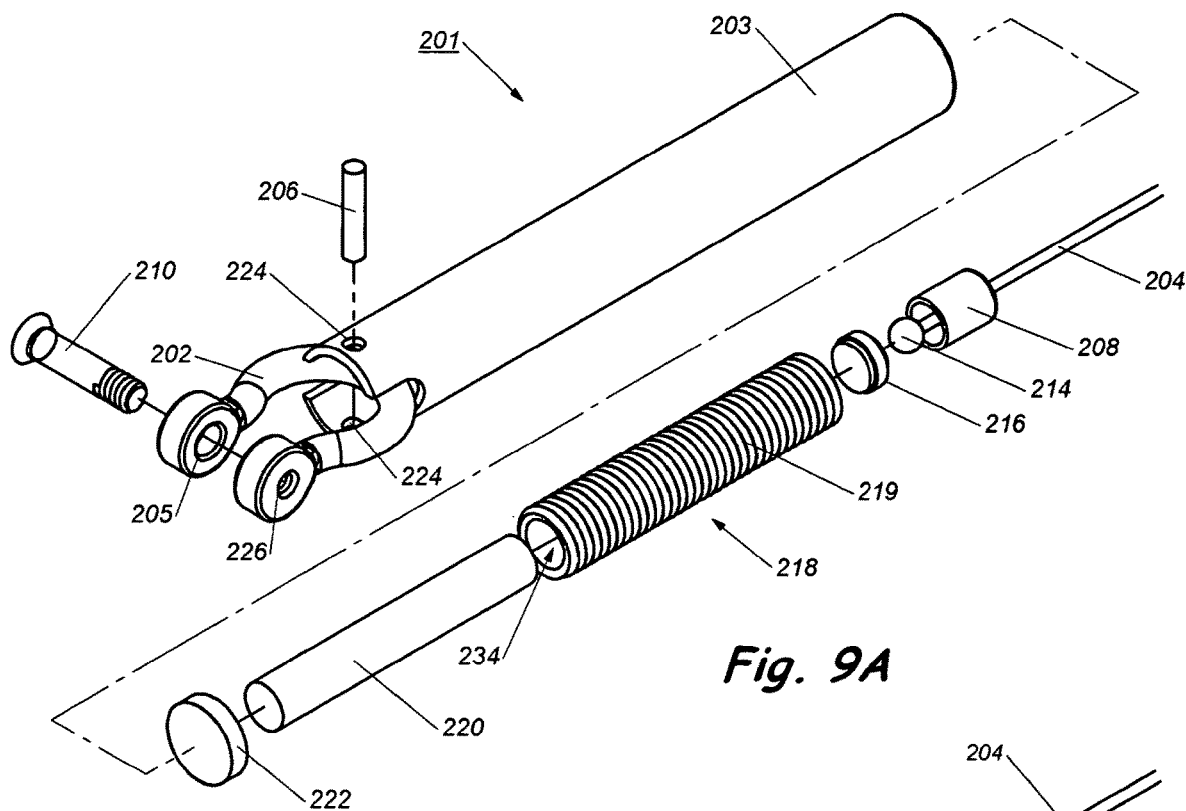
FIG. 9A shows a perspective exploded view of a device according to one embodiment of the present invention.
Figure 9B:
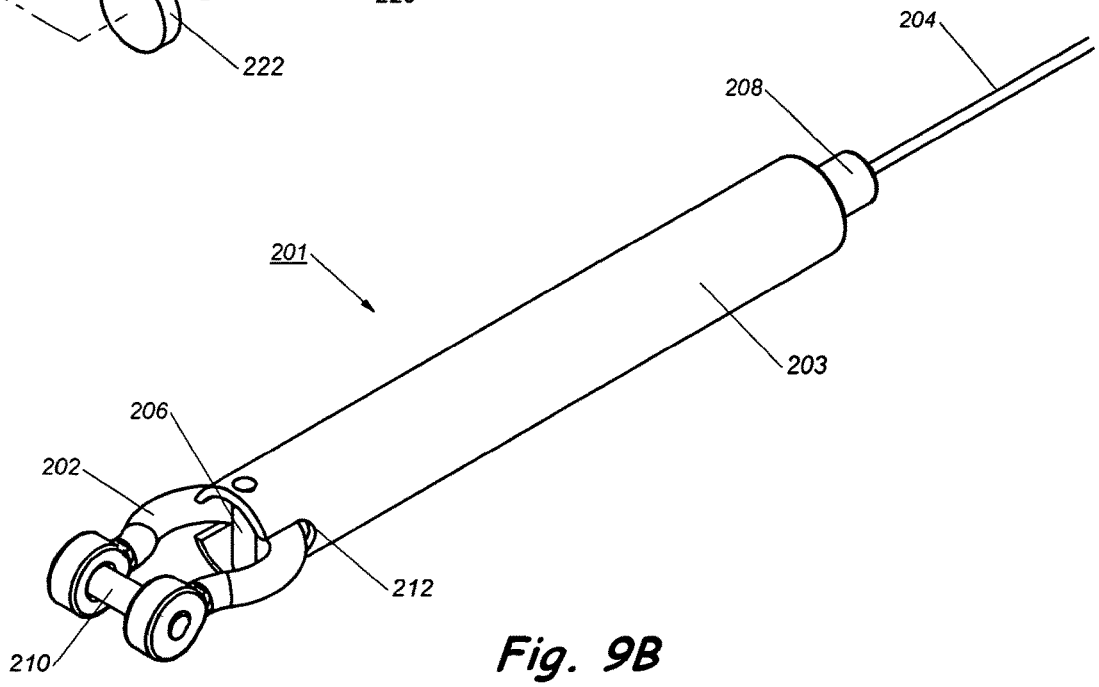
FIG. 9B shows a perspective view of the device shown in FIG. 9A.

FIGS. 6A through 8B show alternative embodiments of guide means for the pelvic bone attachment. FIG. 6A is an exploded, perspective view of the preferred embodiment of the pelvic guide means 900 showing sheath 910 with second flexible member 917 passed through it, and bracket 912 securing sheath 910 to pelvic bone 102 with bone screw 914. FIG. 6B shows the assembled pelvic guide means 900. FIG. 7A is an exploded, perspective view of an alternative embodiment of the pelvic guide means 901, whereby the sheath is replaced by a bracket guide means 960 which guides second flexible member 917. Bracket guide means 960 is attached to pelvic bone 102 with bone screw 914. FIG. 7B shows the assembled pelvic guide means 901. FIG. 8A is an exploded, perspective view of an alternative embodiment of the pelvic guide means 902 whereby a pulley 952 is attached to pelvic bone 102 with a bone screw 914. Pulley 952 will rotate and guide second flexible member 917. FIG. 8B shows the assembled pelvic guide means 902.

FIGS. 9A through 10B show one embodiment of the device 200 whereby actuation means 201 is actuated by a changing magnetic field. Actuation means 201 is shown to consist of a diametrically magnetized magnet 220 which is bonded or otherwise rotationally constrained within a cavity 234 of a tubular leadscrew 218 which has helical threads 219 on its exterior surface. The ends of tubular leadscrew 218 are plugged with a first end cap 222 and a second end cap 216, and this assembly is welded or otherwise hermetically sealed to prevent corrosion of magnet 220. A ball end 214 is swaged onto connection means 204 which is passed through a hole in a bearing cap 208. Bearing cap 208 is then welded or otherwise permanently attached to second end cap 216. Connection means 204 should therefore be able to rotate freely relative to the rest of the assembly. A shackle 202 is attached to a housing 203 with a pin 206. Shackle 202 should be able to rotate about both axes which are orthogonal to the axis of housing 203, thereby allowing alignment of actuation means 201 between pelvic bone 104 and vertebra 100. The inside of housing 203 is threaded to match the threads of tubular leadscrew 218 so that the entire assembly attached to tubular leadscrew 218 can be threaded into housing 203. The assembled device is shown in FIG. 9B.

Figure 10A:
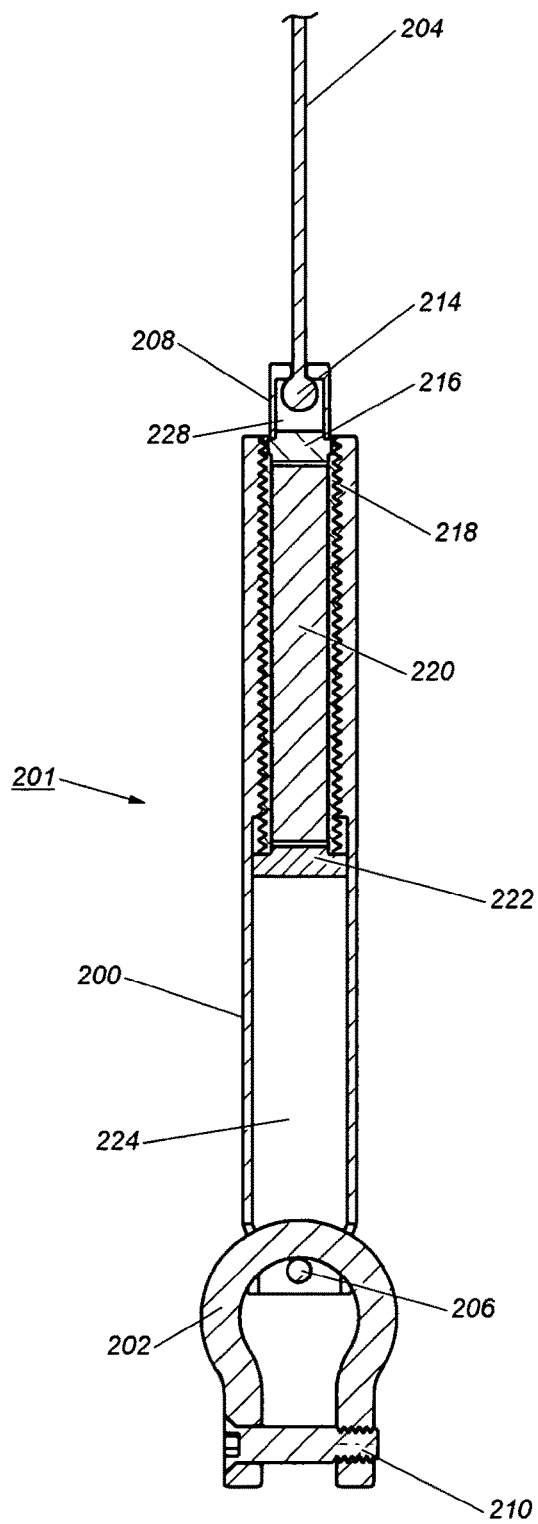
FIG. 10A shows a sectioned view of the device shown in FIGS. 9A and 9B in an extended or "lengthened" configuration.
Figure 10B:
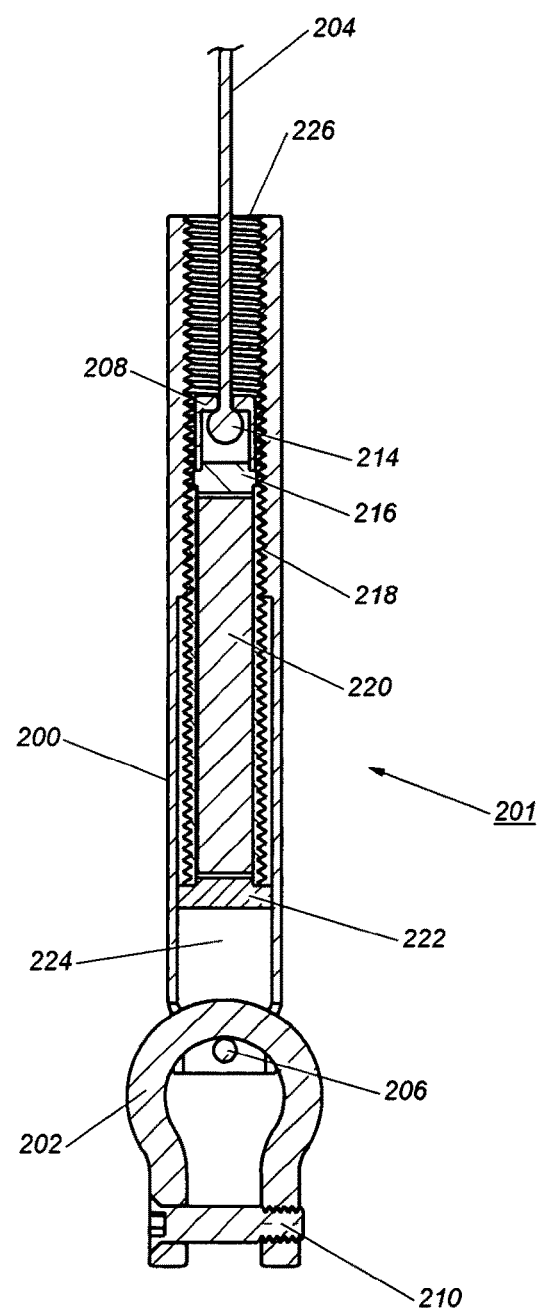
FIG. 10B shows a sectioned view of the device shown in FIGS. 9A and 9B in a retracted or "shortened" configuration.

FIGS. 10A and 10B show a section view of device 200. FIG. 10A shows the 'as implanted' configuration and FIG. 10B shows the device after it has been significantly contracted or "shortened". Tubular leadscrew 218 threads down into housing 203 when turned by magnet 220 which is rotationally constrained within it. Bearing cap 208 allows tubular leadscrew 218 to rotate without twisting connection means 204.

Figure 11A:
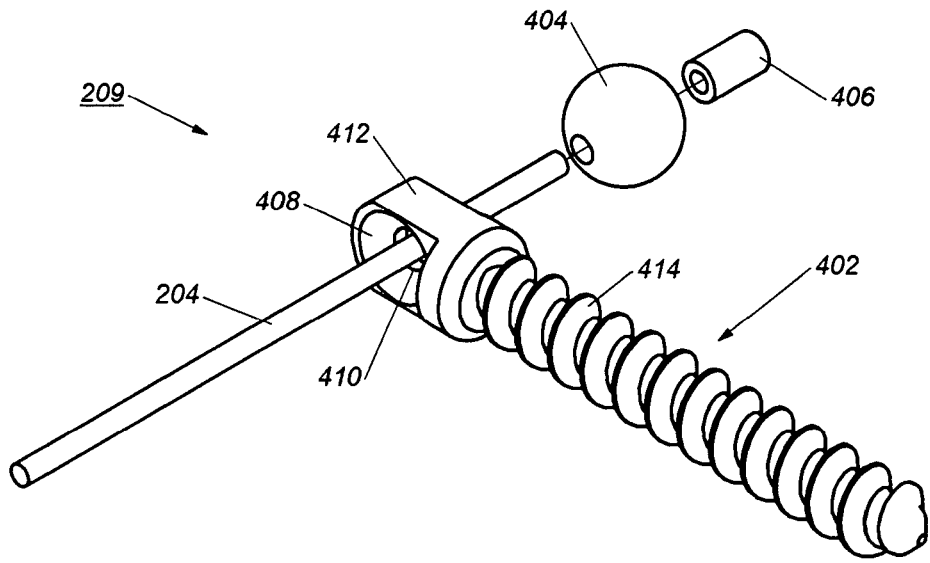
FIG. 11A shows an exploded, perspective view of a spinal attachment member according to one embodiment of the present invention.
Figure 11B:
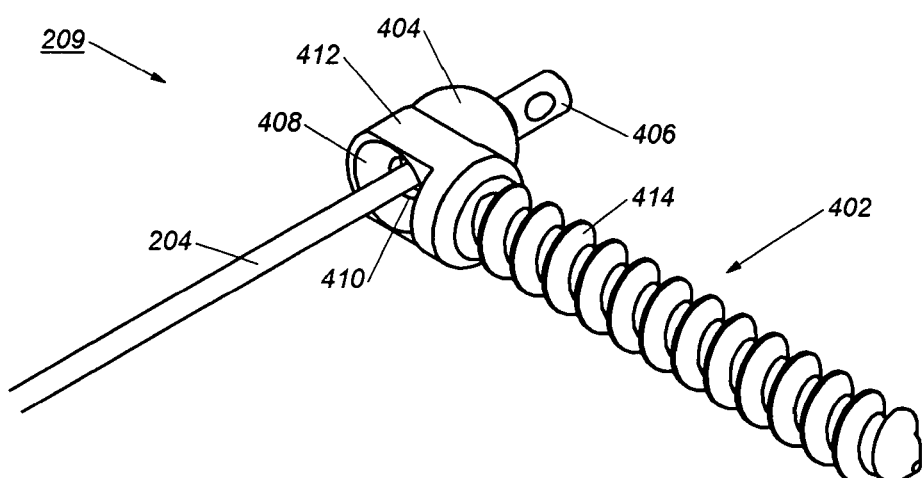
FIG. 11B shows a perspective view of the spinal attachment member shown in FIG. 11A.

FIGS. 11A and 11B show one embodiment of the spinal attachment means 209. A pedicle screw 402 with screw threads 414 for attachment to a pedicle, has a through hole 410 and a spherical recess 408. A ball 404 also has a hole. Flexible member 204 is passed through hole 410 and through the hole in ball 404 and a crimp 406 is secured on the end by crimping or swaging. Crimp 406 could easily be replaced with a swaged stop sleeve, a threaded stud, an eye, a clamp, or other means. Therefore, ball 404 articulates with spherical recess 408 when there are movements of connection means 204. FIG. 11B shows the assembled spinal attachment means 209. This is just one of many possible means to attach connection means 204 to vertebra 100.

Figure 12:
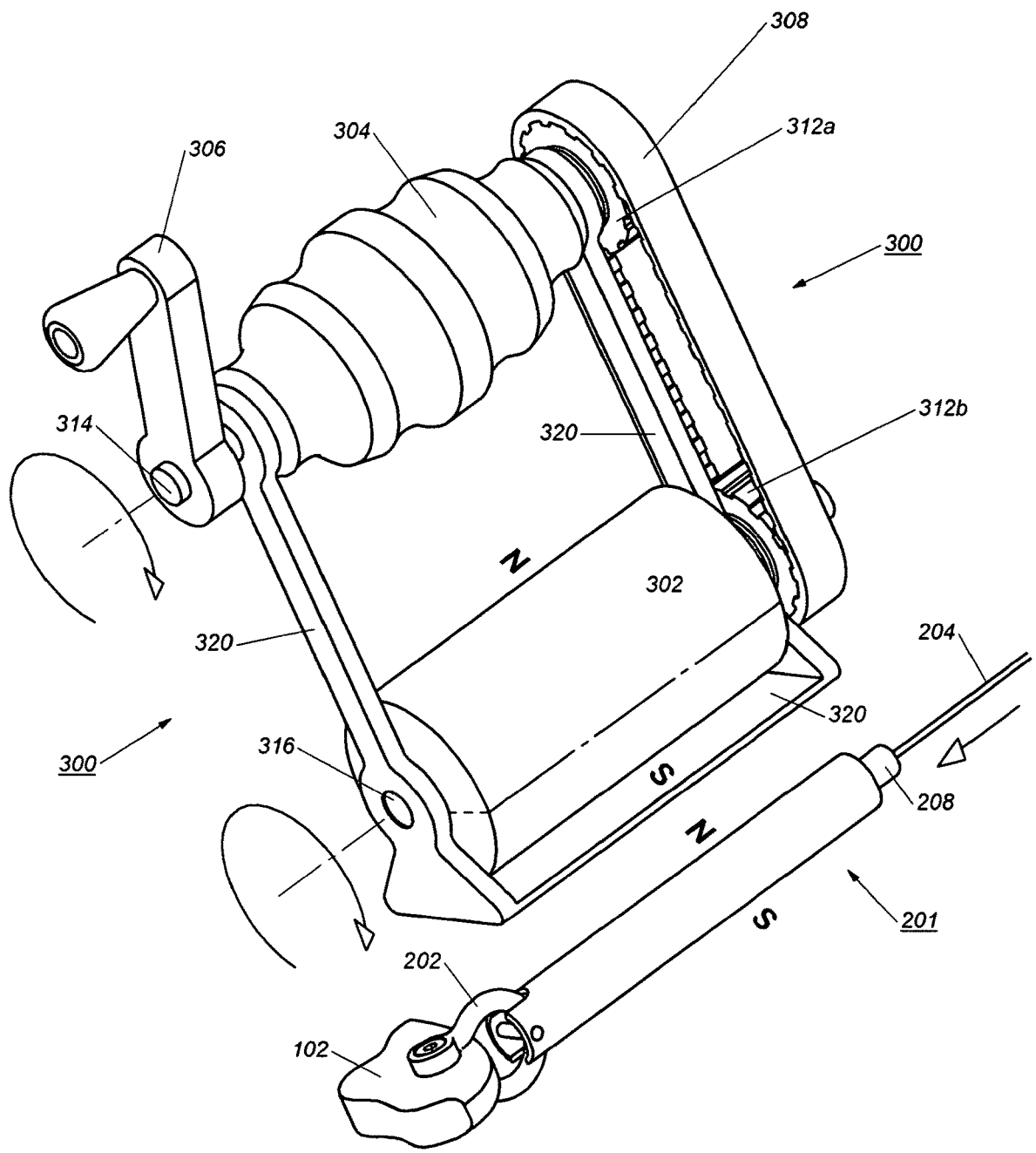
FIG. 12 shows a perspective view of an actuator and a device according to one embodiment of the present invention.
Figure 13:
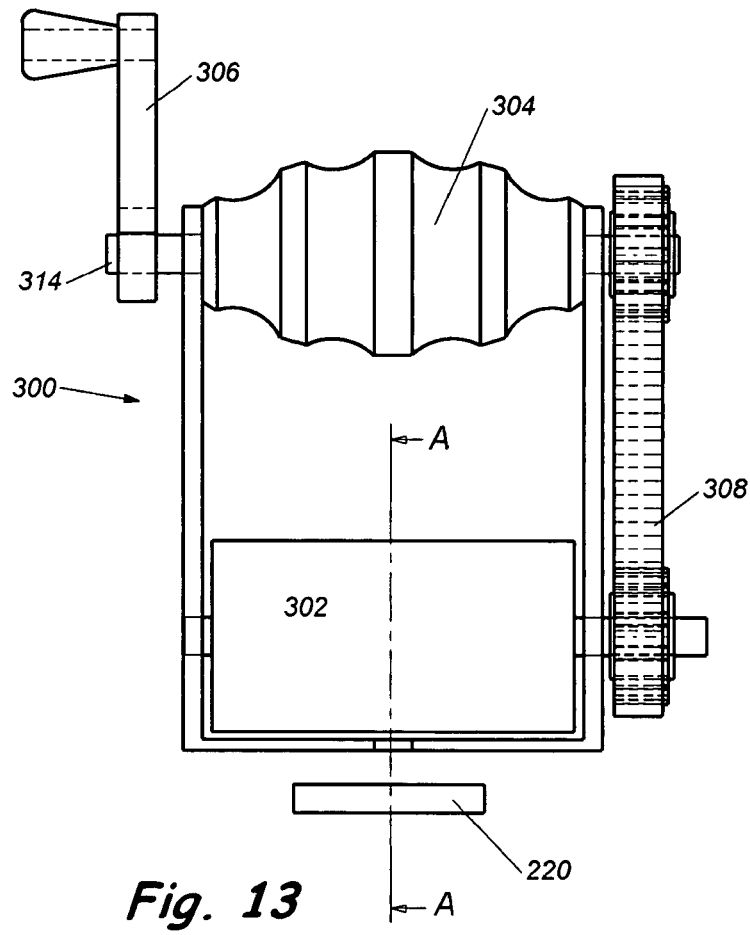
FIG. 13 shows a side view of the actuator and the device shown in FIG. 12.
Figure 14:
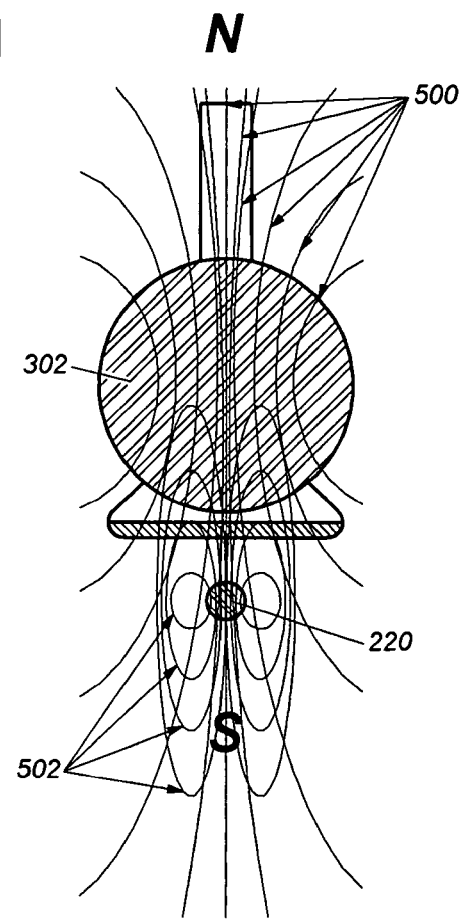
FIG. 14 is a cross-section of the actuator and the device shown in FIGS. 12 and 13 showing magnetic flux lines for both the actuator magnet and the implanted magnet.

FIGS. 12 through 14 show the preferred embodiment of the actuation means 300. A magnet 302, which is diametrically magnetized as indicated on the figure by the north (N) and south (S) poles, is rigidly fixed to a first axle 316 which rotates within a frame 320. A handle 304 is connected to frame 320. A crank 306 is rigidly fixed to a second axle 314 which is also rigidly fixed to a first pulley 312a. A belt 308 wraps around first pulley 312a and a second pulley 312b which is rigidly fixed to the same axle 316 to that which magnet 302 is fixed. Rotation of crank 306 will rotate first pulley 312a and second pulley 312b (by the action of belt 308) which rotates axle 316 and therefore magnet 302. This action is shown schematically by the arrows in the figure. In short, rotation of crank 306 rotates magnet 302. There are many ways to rotate a magnet and this single example is not meant to limit the scope of the invention.

Actuation means 300 is positioned so that frame 320 is nearby, or in contact with, the patient's skin and magnet 302 is aligned approximately parallel to housing 203. Magnet 302 has a magnetic field shown by magnetic flux lines 500 in FIG. 14. This magnetic field interacts with a magnetic field (shown by magnetic flux lines 502) generated by magnet 220. Opposite poles (NS or SN) tend to attract and like poles (NN or SS) tend to repel. Therefore, rotation of one diametrically magnetized magnet situated roughly parallel to a second diametrically magnetized magnet will cause rotation of the second magnet. In short, rotation of crank 306 rotates magnet 302 which rotates magnet 220 within device 200 by magnetic attraction and repulsion. In this way, device 200 can be actuated non-invasively. If external magnet 302 turns without turning the implanted magnet 220, there will be a significant rotational resistance as like poles of the two magnets pass by each other. Therefore, there is feedback inherent to the system to tell the operator if the device 200 is functioning correctly.

An electromagnet may be substituted for the permanent magnet 302. The electromagnet could produce a static magnetic field and then be physically rotated, or the field created could be a dynamic field that does not require physical rotation. Instead of manually turning permanent magnet 302, a motorized device could be used which might contain a control system to measure the rotational resistance described above and warn the operator in the case of improper operation.

Figure 15:
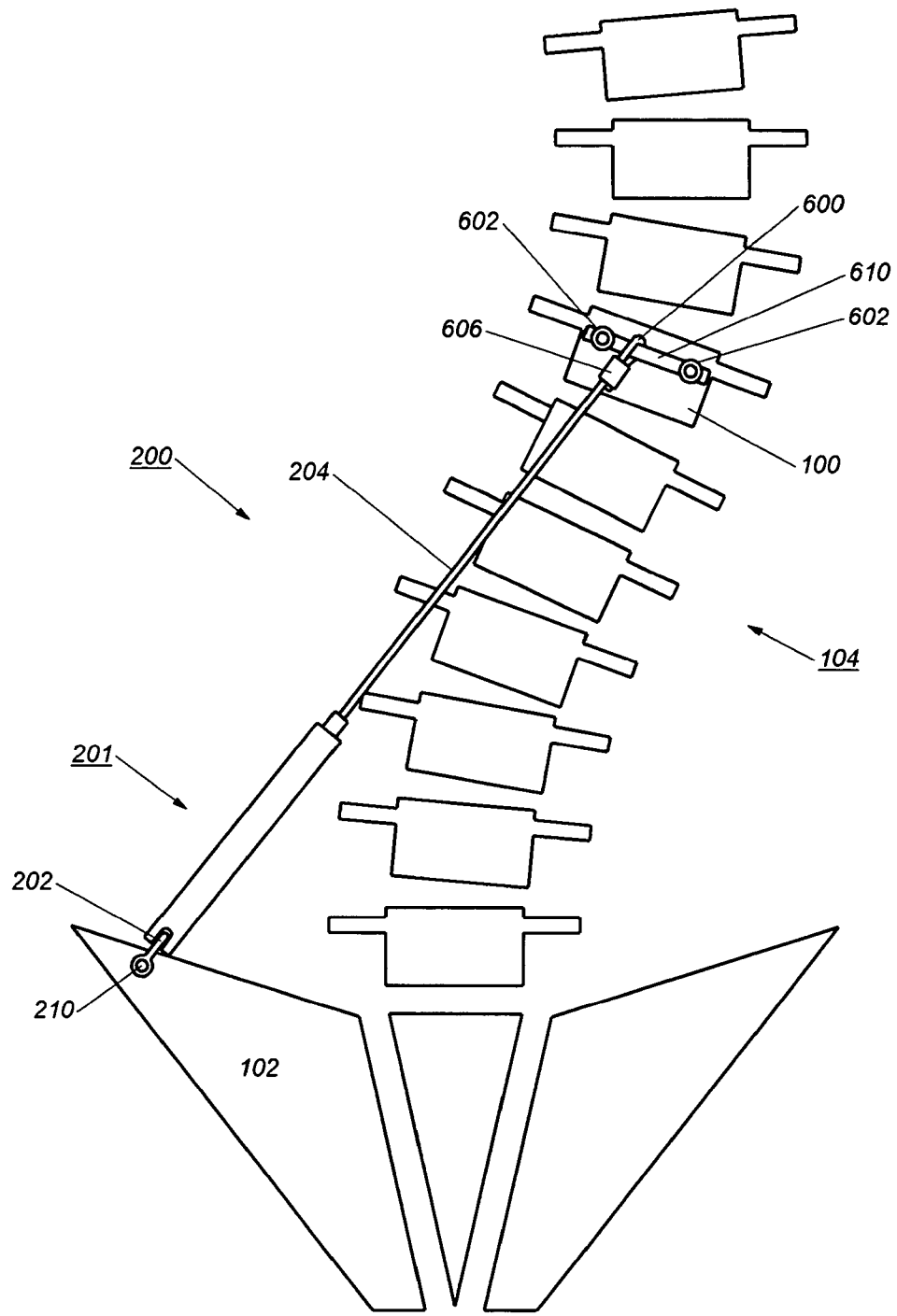
FIG. 15 shows schematically a posterior view of a deformed human spine with an implanted device according to another embodiment of the present invention.
Figure 16:
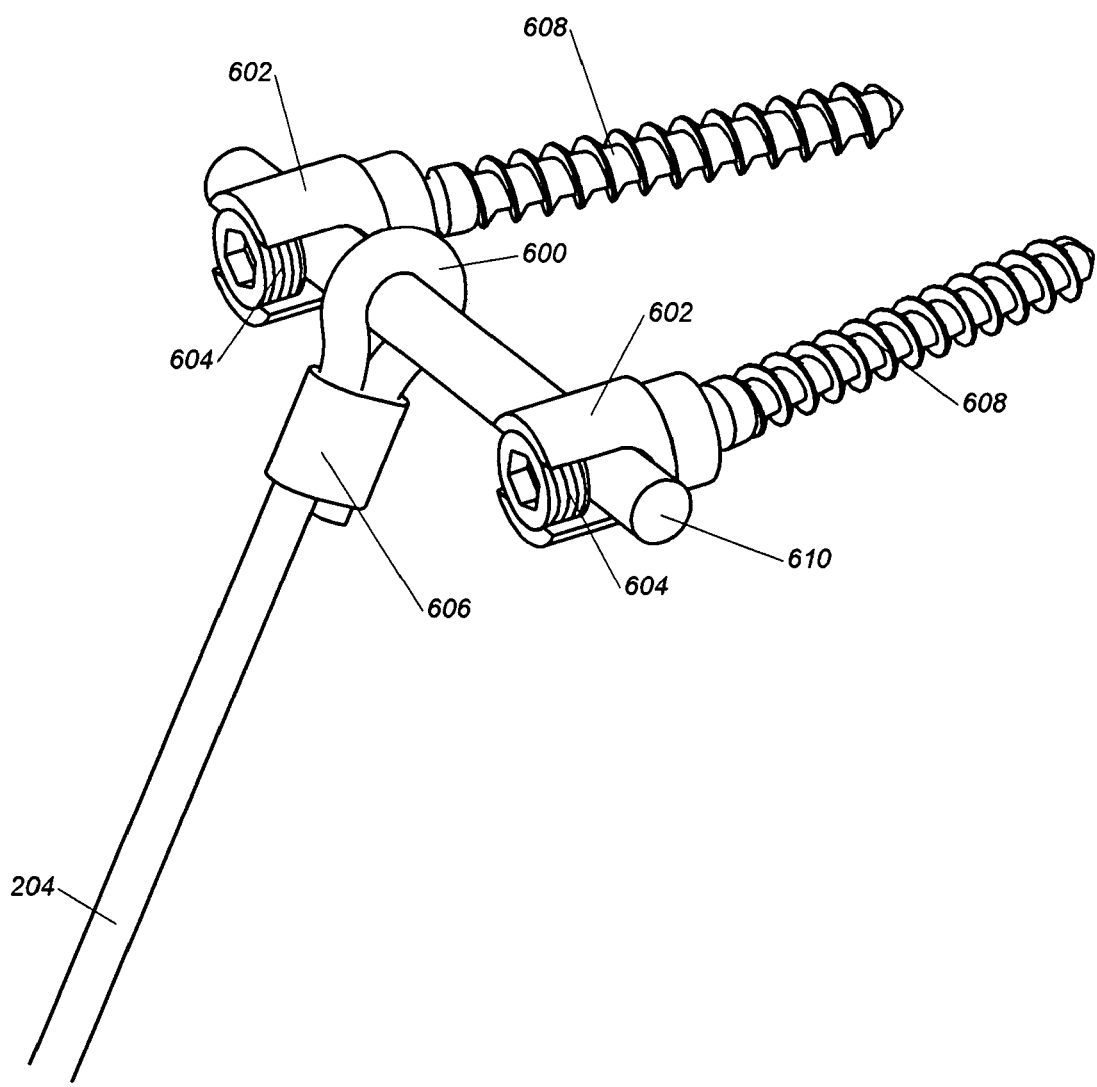
FIG. 16 is a detail, perspective view of an alternative embodiment of the spinal attachment member.
Figure 17A:
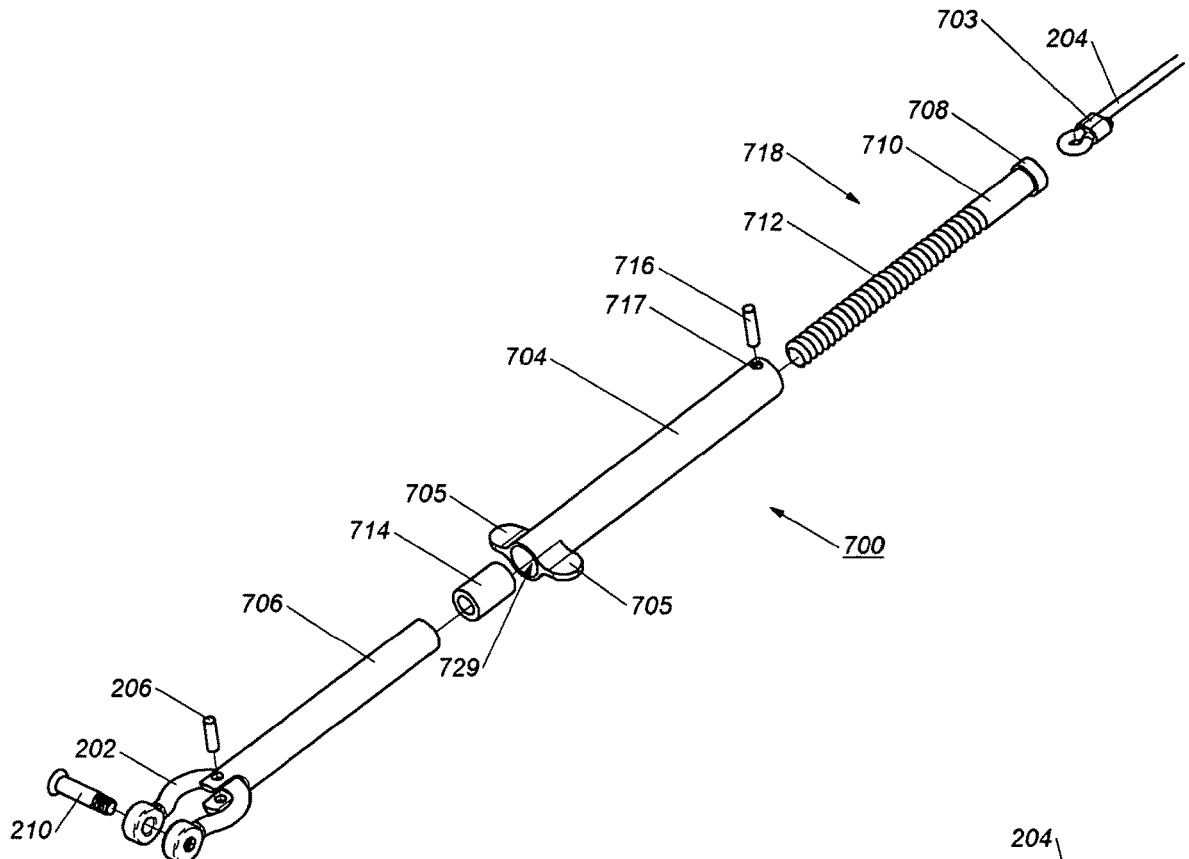
FIG. 17A is an exploded, perspective view of a device according to another embodiment of the present invention.
Figure 17B:
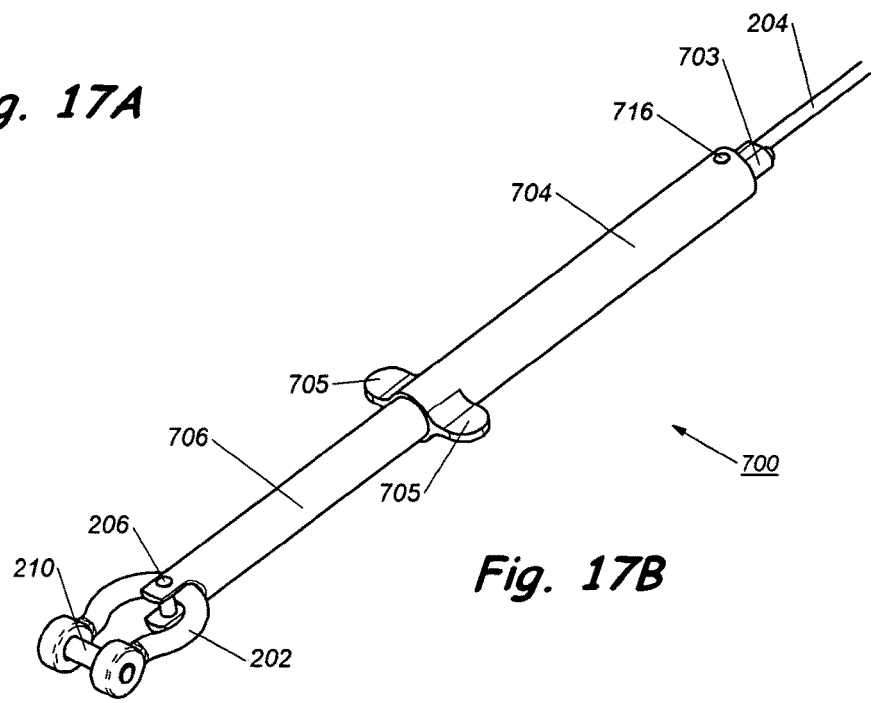
FIG. 17B is a perspective view of the device shown in FIG. 17A.

FIG. 15 shows a schematic representation of a deformed spine with another alternative embodiment of the device 200. FIG. 16 shows the spinal attachment means in greater detail. Two pedicle screws 608 are shown locked to a bar 610 with set screws 604 to form a rigid construct that is well anchored to the spine. Connection means 204 is looped around bar 610 and secured by a crimp 606. A thimble may be incorporated to reduce abrasion of connection means 204. Alternatively, connection means 204 may be secured to bar 610 with a clamp or other securing means or may be tied with a knot.

FIGS. 17A through 18B show an alternative embodiment of the device 700. A loop is formed in connection means 204 which is held in place with a crimp or swage 703. A housing 704 has a pin 716 which is pushed through the loop in connection means 204 to permanently secure connection means 204 to housing 704. The opposite end of connection means 204 is attached to the spine (not pictured) as described above. Housing 704 has wings 705, a pin hole 717, a first bore 729 and a second bore 730. Leadscrew 718 has a head 708, a shank 710, and a right-hand threaded portion 712. Leadscrew 718 is slid into second bore 730 until head 708 abuts the bottom of second bore 730, and a one-way clutch 714 is slid into first bore 729 over threaded portion 712 and onto shank 710 as shown in FIGS. 15 & 16. One-way clutch 714 will allow housing 704 to rotate counter-clockwise, but will rotationally lock housing 704 to leadscrew 718 when housing 704 is rotated clockwise. A threaded housing 706 is threaded onto leadscrew 718. When one of wings 705 is pressed, housing 705 is rotated. If the resulting rotation is clockwise, leadscrew 718 advances into threaded housing 706, drawing threaded housing 706 into housing 704, thereby shortening the overall length of the device 700. If the rotation is counter-clockwise, housing 704 free-wheels on one-way clutch 714 and leadscrew 718 is not rotated. Therefore, pressing alternately on wings 705 will shorten device 700. Alternatively, leadscrew 718 may have left-hand threads and one-way clutch 714 may engage when housing 704 is rotated counter-clockwise, achieving the same effect as stated above. Since device 700 is implanted just under the skin, pressing on the patient's skin from outside the body will cause shortening of device 700 non-invasively.

Figure 19A:
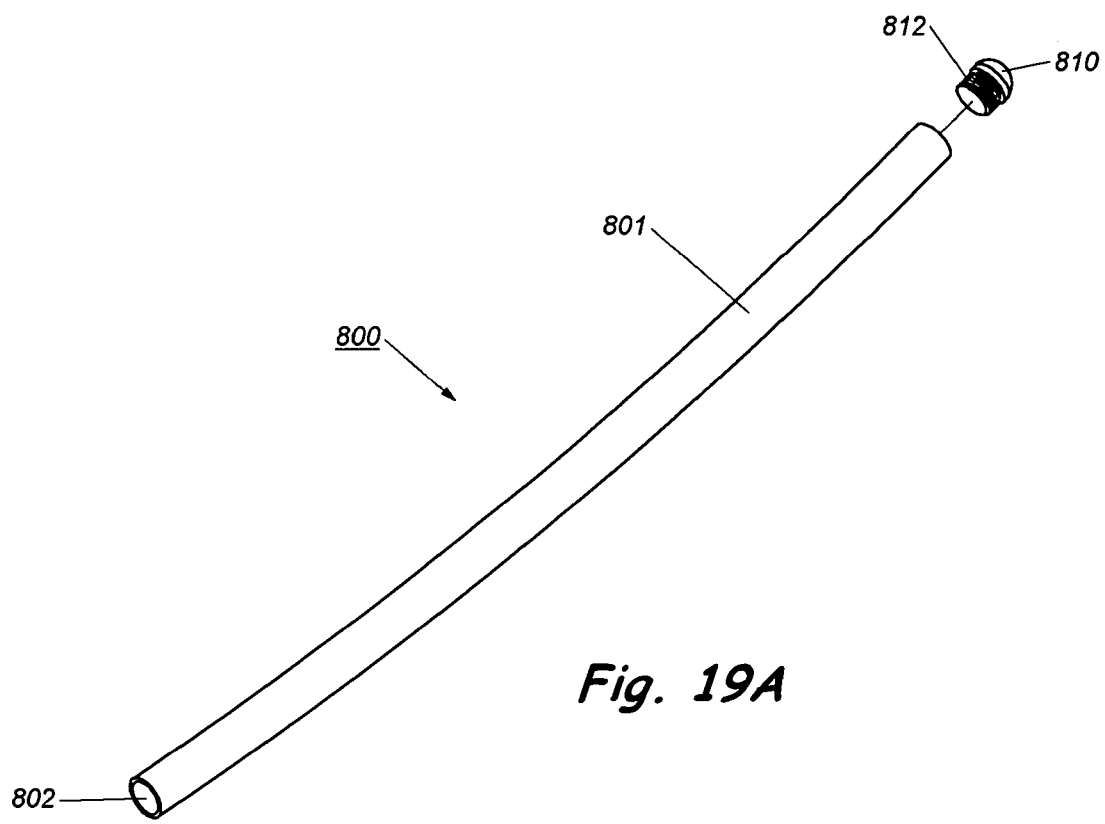
FIG. 19A shows an exploded perspective view of one embodiment of an instrument used for implantation of the device.
Figure 19B:
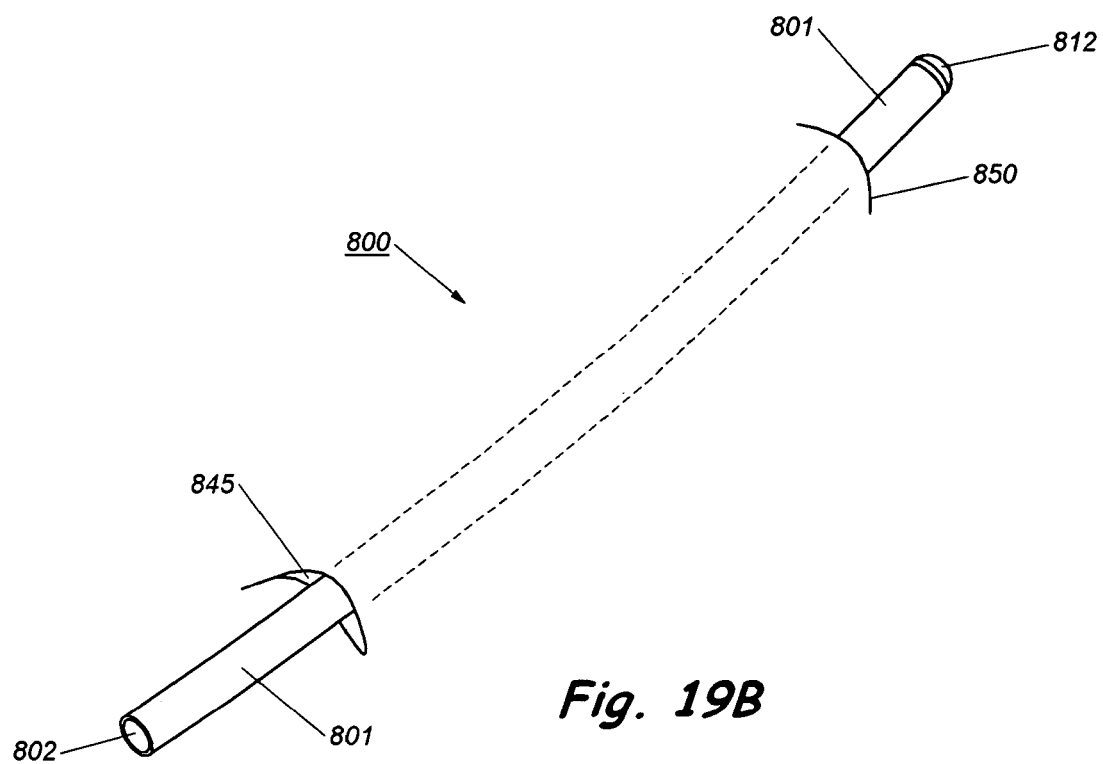
FIG. 19B shows a perspective view of the instrument shown in FIG. 19A in use during implantation surgery.

FIGS. 19A and 19B show an instrument means 800 for implanting device 200, device 700, or tether 280. Instrument means 800 consists of an elongated tube 801, and a cap 810 with threads 812 which engage matching threads within the end of elongated member 801. A pelvic incision 845 and a spinal incision 850 are made at the site(s) planned for pelvic attachment or guide(s) and site(s) planned for spinal attachment or guide(s), respectively, of device 200, device 700 or tether 280. Instrument means 800 is introduced into one of these incisions and is manipulated by the surgeon until it reaches the other incision and has created a tunnel which will accommodate the appropriate implant(s). The cap is then removed and the implant(s) is fed into elongated tube 801 so that the ends of the implant(s) are present at the incisions and can be handled by the surgeon. Instrument 800 may then be removed. Instrument 800 can have any cross-sectional shape, can be curved or straight, and can be made from a surgical grade metal, polymer, ceramic, or composite, and may be a disposable item.

Figure 20A:
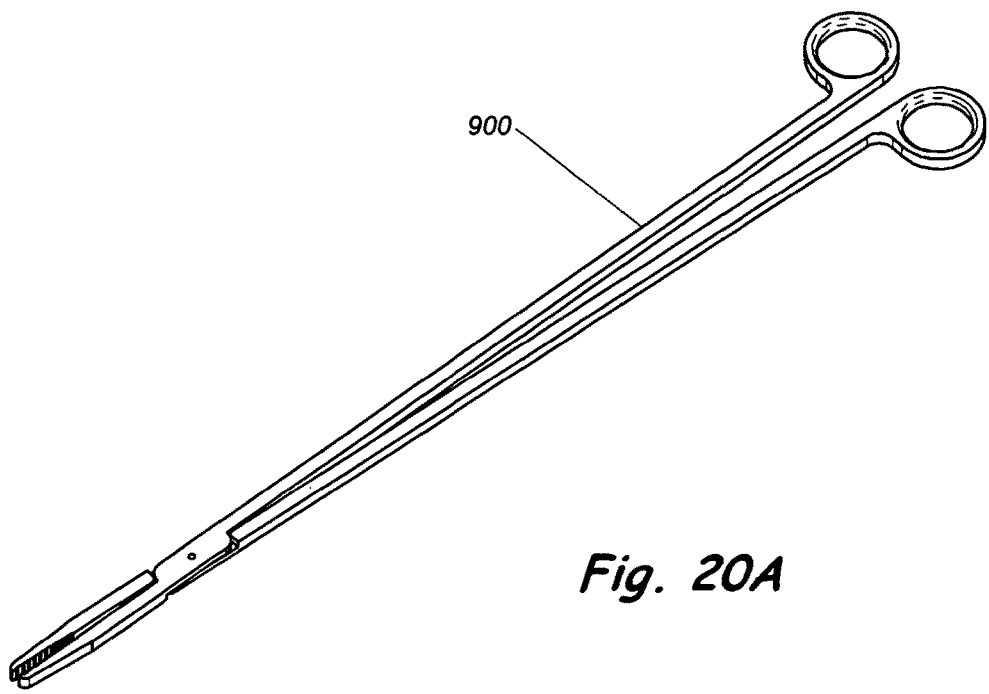
FIG. 20A shows an exploded perspective view of an alternative embodiment of an instrument used for implantation of the device.
Figure 20B:
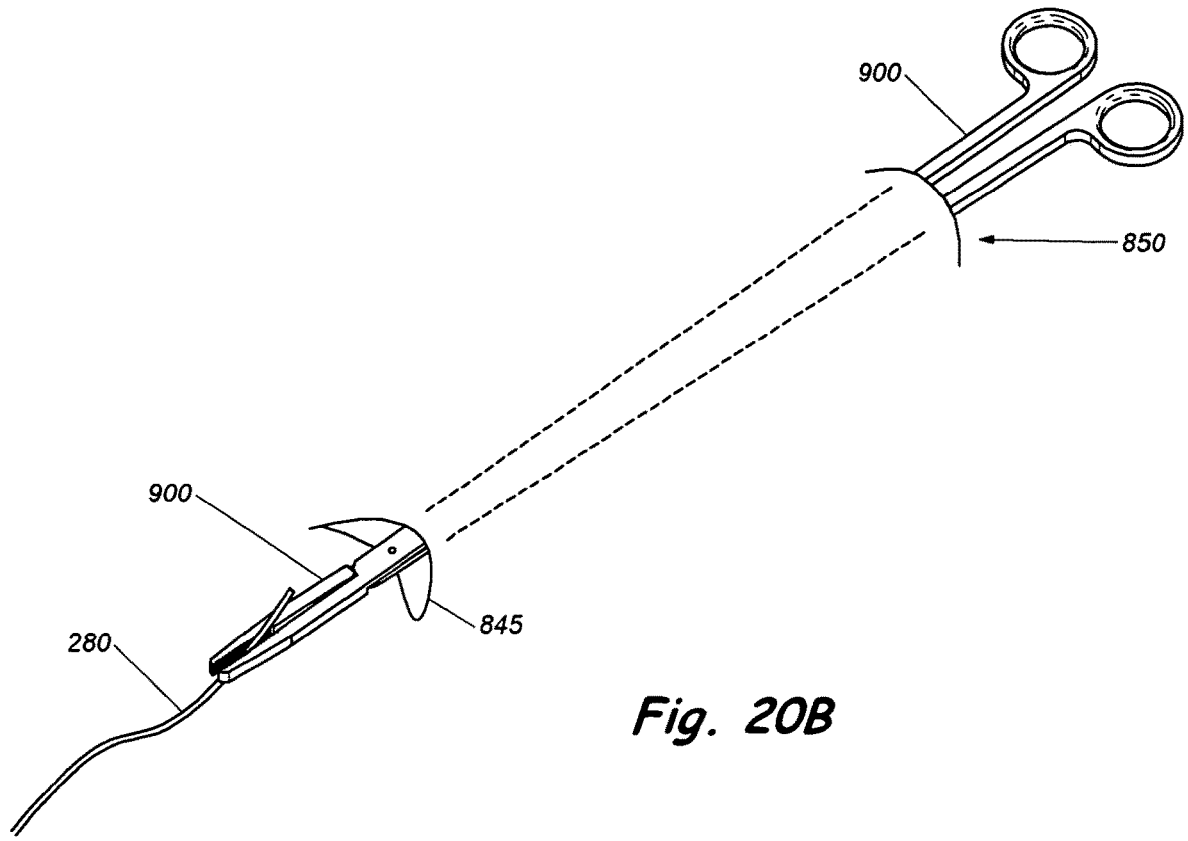
FIG. 20B shows a perspective view of the instrument shown in FIG. 20A in use during implantation surgery.

FIGS. 20A and 20B show an alternative instrument means for implanting device 200, device 700, or tether 280. A pelvic incision 845 and a spinal incision 850 are made at the site(s) planned for pelvic attachment or guide(s) and site(s) planned for spinal attachment or guide(s), respectively, of device 200, device 700 or tether 280. Forceps 900 are introduced into one incision and are manipulated by the surgeon until reaching the other incision. One end of the implant(s) is grabbed with forceps 900 and the implant(s) is pulled to the other incision.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A method for treatment of spinal deformity of a patient comprising:
    providing an adjust device including:
        a housing;
        a rod having one end received in the housing and the other end extending outwardly from the housing; and
        a first magnet connected to the housing and configured to adjust a length of the rod;
    attaching one part of the rod to a first bone and a second part of the rod to a second bone, wherein the first bone is a pelvic bone and the second bone is a vertebra;
    positioning an actuator above a skin of the patient, the actuator having a second magnet;
    while the actuator is positioned above the patient skin, producing a magnetic field with the second magnet that interacts with the first magnet to cause the rod to extend out from the housing; and
    wherein the step of producing a magnetic field with the second magnet causes rotation of the first magnet which causes rotation of a leadscrew within the housing, whereby rotation of the leadscrew causes translation of the rod thereby changing a length of an exposed portion of the rod.

2. The method of claim 1, wherein the step of producing the magnetic field with the second magnet causes rotation of the first magnet which causes rotation of the leadscrew within the housing, an outer thread of the leadscrew engaging an inner thread of the housing to cause translation of the rod thereby changing a length of the exposed portion of the rod.

3. The method of claim 1, wherein the step of attaching the second part of the rod includes:
    inserting a pedicle screw into the second bone; and
    attaching the second part of the rod to the inserted pedicle screw.

4. The method of claim 1, wherein the first magnet is received within the leadscrew.

5. The method of claim 1, wherein the first magnet is positioned between a distal end of the housing and a proximal end of the leadscrew.

6. The method of claim 5, wherein the second magnet rotates via a plurality of pulleys.

7. The method of claim 3, wherein inserting a pedicle screw includes inserting two pedicles screws into the vertebra and attaching the second part of the rod to the two inserted pedicle screws.

8. A method for treatment of spinal deformity of a patient comprising:
    providing an adjust device including:
        a housing;
        a rod having one end received in the housing and the other end extending outwardly from the housing, the rod having a first length;
        a lead screw coupled to the rod; and
        a first magnet attached to the housing;
        wherein the adjustment device is insertable into the patient;
    attaching the adjustment device to a first bone and a second bone for treating spinal deformity, wherein the first bone is a pelvic bone and the second bone is a vertebra;
    positioning an actuator above a skin of the patient, the actuator having a second magnet;
    while the actuator is positioned above the patient skin, creating a changing magnetic field by the second magnet which rotates the first magnet, whereby rotation of the first magnet causes rotation of the lead screw, whereby rotation of the lead screw causes translation of the rod such that the adjustment device changes from the first length to a second length longer than the first length.

9. The method of claim 8, wherein the housing comprises inner threads.

10. The method of claim 9, wherein the lead screw comprises outer threads that engage with the inner threads of the housing.

11. The method of claim 8, wherein the first magnet is positioned between a distal end of the housing and a proximal end of the lead screw.

12. The method of claim 11, wherein the rod comprises an end portion having a diameter greater than a middle portion.

13. The method of claim 8, wherein creating the changing magnetic field includes rotating the second magnet.

14. The method of claim 13, wherein the second magnet is rotated via a plurality of pulleys.

15. The method of claim 13, wherein the adjustment device is attachable to the first bone via one or more pedicle screws.

\* \* \* \* \*